United States Patent
Den Boef et al.

(10) Patent No.: US 8,830,472 B2
(45) Date of Patent: Sep. 9, 2014

(54) METHOD OF ASSESSING A MODEL OF A SUBSTRATE, AN INSPECTION APPARATUS AND A LITHOGRAPHIC APPARATUS

(75) Inventors: Arie Jeffrey Den Boef, Waalre (NL); Hugo Augustinus Joseph Cramer, Eindhoven (NL); Marcus Adrianus Van De Kerkhof, Helmond (NL); Henricus Petrus Maria Pellemans, Veldhoven (NL); Martin Ebert, Valkenswaard (NL)

(73) Assignee: ASML Netherlands B.V., Veldhoven (NL)

( * ) Notice: Subject to any disclaimer, the term of this patent is extended or adjusted under 35 U.S.C. 154(b) by 934 days.

(21) Appl. No.: 12/920,984

(22) PCT Filed: Mar. 30, 2009

(86) PCT No.: PCT/EP2009/002300
§ 371 (c)(1),
(2), (4) Date: Oct. 22, 2010

(87) PCT Pub. No.: WO2009/124669
PCT Pub. Date: Oct. 15, 2009

(65) Prior Publication Data
US 2011/0026032 A1    Feb. 3, 2011

Related U.S. Application Data

(60) Provisional application No. 61/071,034, filed on Apr. 9, 2008.

(51) Int. Cl.
*G01N 21/55*    (2014.01)
*G01N 21/956*   (2006.01)
*G01N 21/95*    (2006.01)
*G03F 7/20*     (2006.01)
*G01N 21/47*    (2006.01)
*G01N 21/88*    (2006.01)

(52) U.S. Cl.
CPC ...... *G01N 21/9501* (2013.01); *G01N 21/95607* (2013.01); *G01N 21/47* (2013.01); *G01N 2021/8845* (2013.01); *G03F 7/70625* (2013.01)

USPC .............. 356/446; 356/237.1; 356/239.3; 356/237.3

(58) Field of Classification Search
CPC ........................................ G01J 3/45
USPC ........................... 356/237.1–239.3
See application file for complete search history.

(56) References Cited

U.S. PATENT DOCUMENTS 5,216,257 A    6/1993    Brueck et al.
6,458,605 B1   10/2002   Stirton
(Continued)

FOREIGN PATENT DOCUMENTS

CN    1916603 A      2/2007
EP    1 628 164 A2   2/2006
(Continued)

OTHER PUBLICATIONS

International Preliminary Report on Patentability and Written Opinion mailed Oct. 21, 2010, directed to International Patent Application No. PCT/EP2009/002300, The International Bureau of WIPO, Geneva, Switzerland; 10 pages.
(Continued)

*Primary Examiner* — Gregory J Toatley
*Assistant Examiner* — Iyabo S Alli
(74) *Attorney, Agent, or Firm* — Sterne, Kessler, Goldstein & Fox P.L.L.C.

(57) ABSTRACT

A method of assessing a model of a substrate is presented. A scatterometry measurement is taken using radiation at a first wavelength. The wavelength of the radiation is then changed and a further scatterometry measurement taken. If the scatterometry measurements are consistent across a range of wavelengths then the model is sufficiently accurate. However, if the scatterometry measurements change as the wavelength changes then the model of the substrate is not sufficiently accurate.

15 Claims, 5 Drawing Sheets

(56) References Cited

U.S. PATENT DOCUMENTS

| | | | |
|---|---|---|---|
| 6,524,163 | B1 | 2/2003 | Stirton |
| 6,639,663 | B1 | 10/2003 | Markle et al. |
| 6,650,422 | B2 | 11/2003 | Singh et al. |
| 6,762,111 | B2 | 7/2004 | Fukuda |
| 6,768,543 | B1 * | 7/2004 | Aiyer .................. 356/237.4 |
| 7,476,856 | B2 | 1/2009 | Watanabe et al. |
| 7,532,305 | B2 | 5/2009 | Den Boef et al. |
| 7,564,555 | B2 | 7/2009 | Den Boef et al. |
| 7,791,712 | B2 | 9/2010 | Den Boef et al. |
| 7,916,284 | B2 | 3/2011 | Dusa et al. |
| 8,054,467 | B2 * | 11/2011 | Den Boef et al. ............. 356/456 |
| 2003/0223630 | A1 | 12/2003 | Adel et al. |
| 2005/0018190 | A1 | 1/2005 | Sezginer et al. |
| 2005/0195413 | A1 | 9/2005 | Brill |
| 2006/0117293 | A1 | 6/2006 | Smith et al. |
| 2007/0296960 | A1 | 12/2007 | Den Boef et al. |
| 2008/0024766 | A1 | 1/2008 | Mieher et al. |

FOREIGN PATENT DOCUMENTS

| | | |
|---|---|---|
| JP | 2003-224057 A | 8/2003 |
| JP | 2005-017145 A | 1/2005 |
| JP | 2005-509132 A | 4/2005 |
| JP | 2006-138754 A | 6/2006 |
| JP | 2007-266601 A | 10/2007 |
| JP | 2008-047900 A | 2/2008 |
| TW | 200813654 A | 3/2008 |

OTHER PUBLICATIONS

International Search Report directed to related International Patent Application No. PCT/EP2009/002300, mailed Jul. 22, 2009; 2 pages.

English-Language Abstract for Japanese Patent Publication No. 2006-138754 A, published Jun. 1, 2006; 1 page.

Borgermans, P., et al., "Dose Reconstruction with Multiple Wavelength Analysis in Irradiated Optical Fibres", Radiation Protection Dosimetry, vol. 85, Nos. 1-4, Nuclear Technology Publishing; pp. 497-500 (1999).

Horn, R. A., et al., "Matrix Analysis", Cambridge University Press; pp. v-vii, 336, 340, 365, 366, 374 and 442 (1985).

Skare, S., et al., "Condition Number as a Measure of Noise Performance of Diffusion Tensor Data Acquisition Schemes with MRI", Journal of Magnetic Resonance, vol. 147, Academic Press; pp. 340-352 (2000).

English-Language Translation of First Office Action directed to related Chinese Patent Application No. 200980109332.0, mailed Jan. 11, 2012, from the State Intellectual Property Office of People's Republic of China; 2 pages.

* cited by examiner

Fig. 2
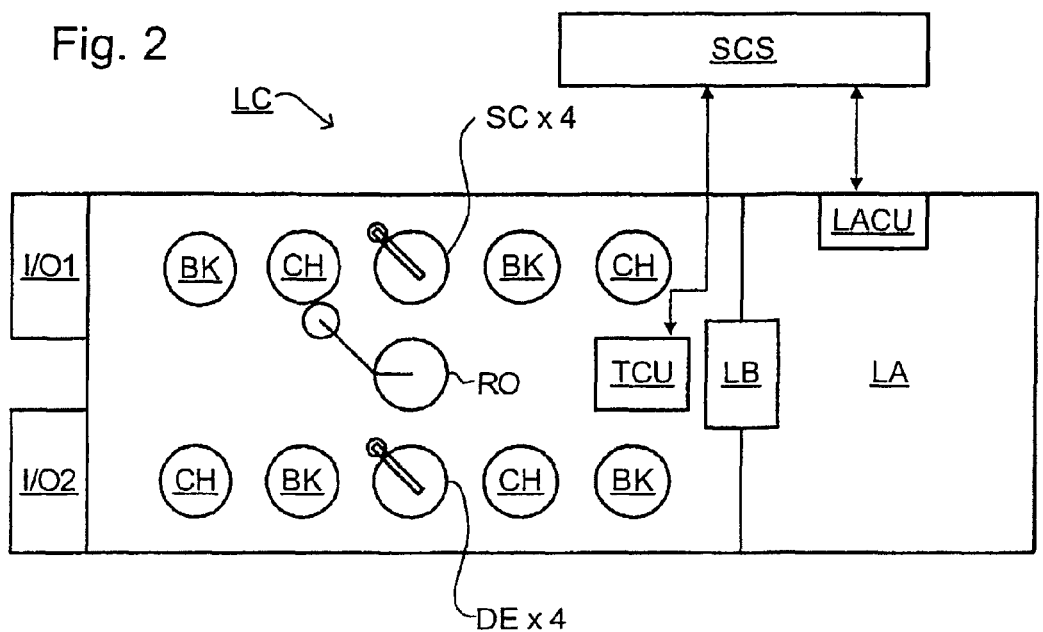
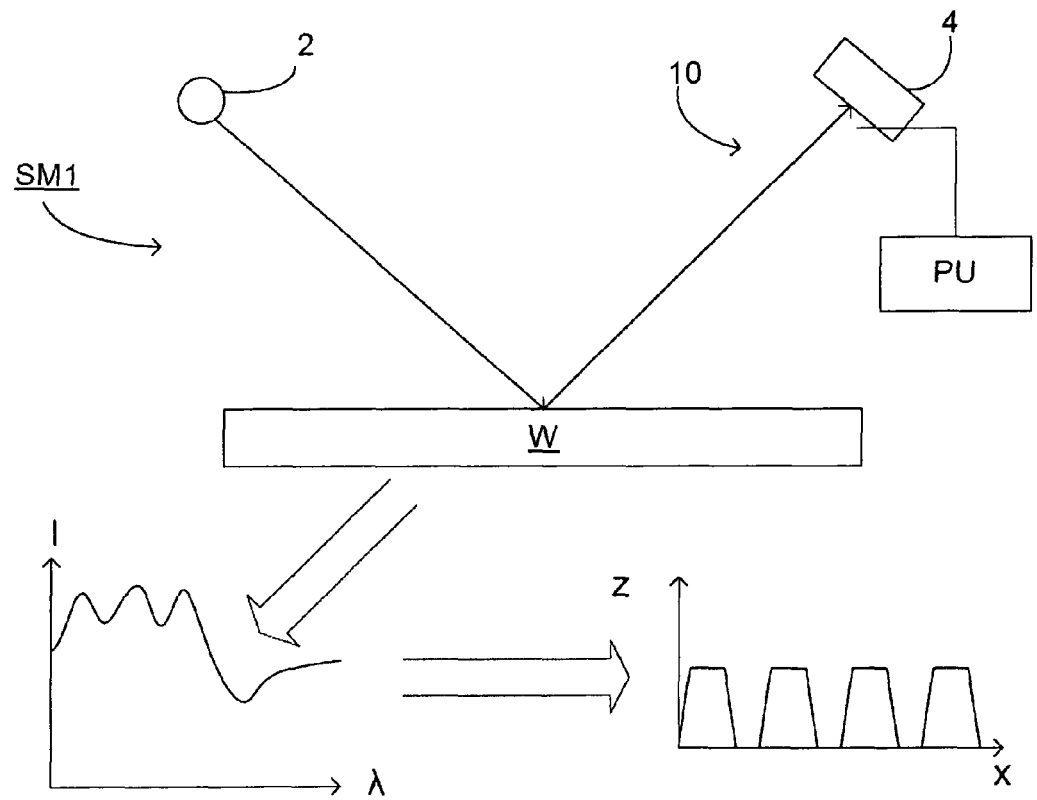
Fig. 3

METHOD OF ASSESSING A MODEL OF A SUBSTRATE, AN INSPECTION APPARATUS AND A LITHOGRAPHIC APPARATUS

FIELD

The present invention relates to methods of inspection usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is desirable to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Scatterometry uses a model of the substrate to measure a feature, for example the side wall angle of a feature. However, if the model of the substrate is inaccurate then large errors will occur in the measured feature. This could occur, for example, if there are line edge roughnesses, which have not been included in the model.

SUMMARY

It is desirable to provide method of assessing the accuracy of the model used in scatterometry.

According to an aspect of the invention, there is provided a method and an apparatus for assessing a model of a feature of a substrate, the method including taking a first scatterometry measurement of the substrate using radiation having known characteristics; determining the value of a characteristic of the feature of the substrate using the scatterometry measurement, the radiation having a first characteristic value; taking a second scatterometry measurement using the radiation having a second characteristic value; determining a second value of the characteristic of the feature using the second scatterometry measurement; and comparing the first value and the second value of the characteristic of the feature to determine the accuracy of the model.

According to a further aspect of the invention there is provided an inspection apparatus and a lithographic apparatus including a radiation projector configured to project radiation onto the substrate, the radiation having a characteristic with a plurality of values; a high numerical aperture lens; and a detector configured to detect the radiation beam reflected from a surface of the substrate; wherein the detector is configured to separate the detected radiation into a plurality of sub-divisions, the radiation of each sub-division having a different value for the characteristic.

According to a further aspect of the invention there is provided an inspection apparatus and a lithographic apparatus including an imaging fourier transform spectrometer.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 2 depicts a lithographic cell or cluster in accordance with an embodiment of the invention;

FIG. 3 depicts a first scatterometer in accordance with an embodiment of the invention;

DETAILED DESCRIPTION

Figure 1:
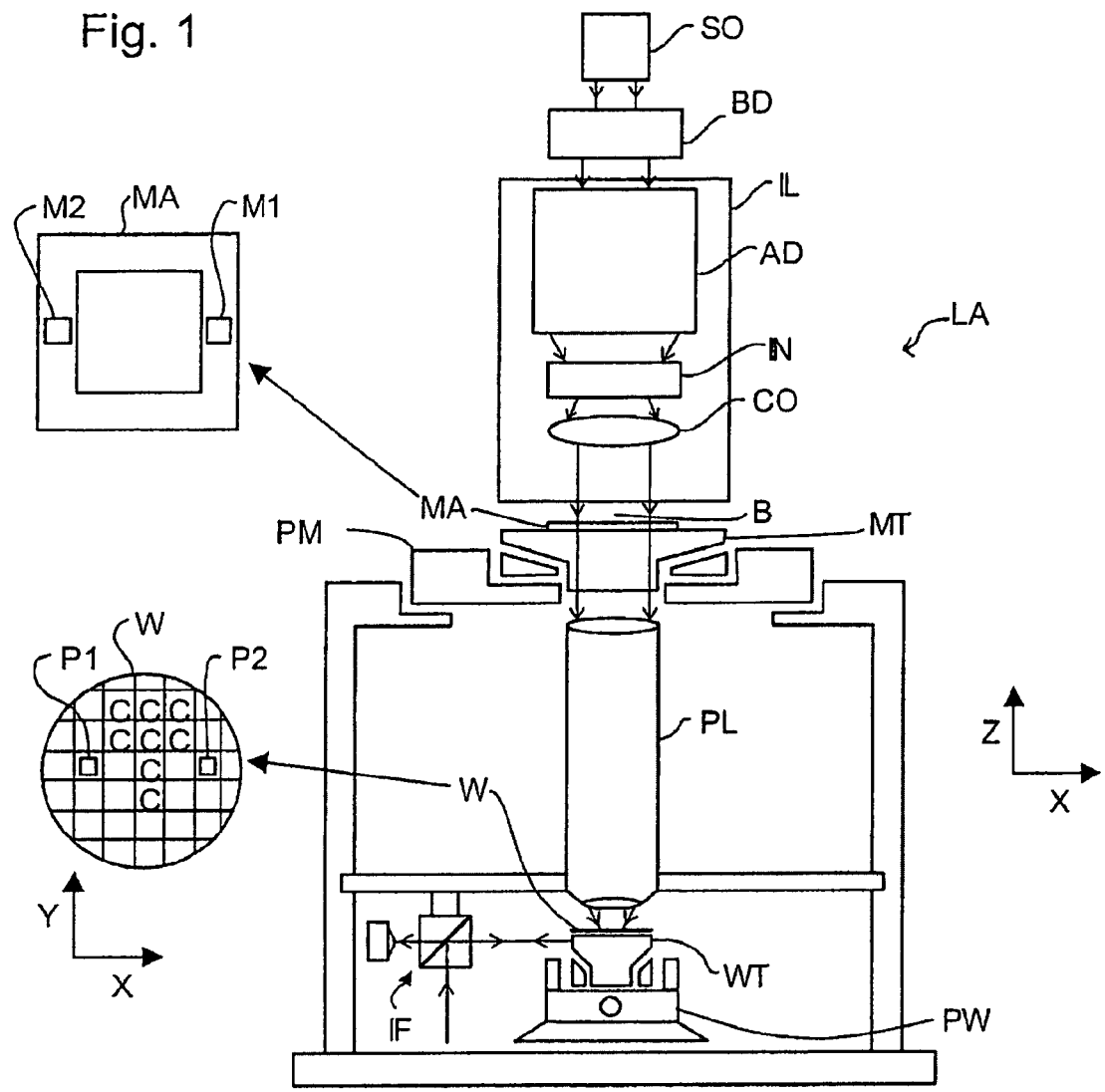
FIG. 1 depicts a lithographic apparatus in accordance with an embodiment of the invention.

FIG. 1 schematically depicts a lithographic apparatus. The apparatus includes an illumination system (illuminator) IL configured to condition a radiation beam B (e.g. UV radiation or DUV radiation); a patterning device support or support structure (e.g. a mask table) MT constructed to support a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support or support structure holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The support structure may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the patterning device support (e.g., mask table) MT, and is patterned by the patterning device. Having traversed the patterning device (e.g. mask) MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device (e.g. mask) MA with respect to the path of the radiation beam B, e.g. after mechanical retrieval from a mask library, or during a scan. In general, movement of the patterning device support (e.g. mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g. mask table) MT may be connected to a short-stroke actuator only, or may be fixed. Patterning device (e.g. mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the patterning device support (e.g. mask table) MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g. mask table) MT and the substrate table WT are scanned synchronously while a pattern imparted to the radiation beam is projected onto a target portion C (i.e. a single dynamic exposure). The velocity and direction of the substrate table WT relative to the patterning device support (e.g. mask table) MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g. mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded—thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a scatterometer SM1 which may be used in an embodiment of the present invention. It includes a broadband (white light) radiation projector 2 which projects radiation onto a substrate W. The reflected radiation is passed to a spectrometer detector 4, which measures a spectrum 10 (intensity (I) as a function of wavelength ($\lambda$)) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
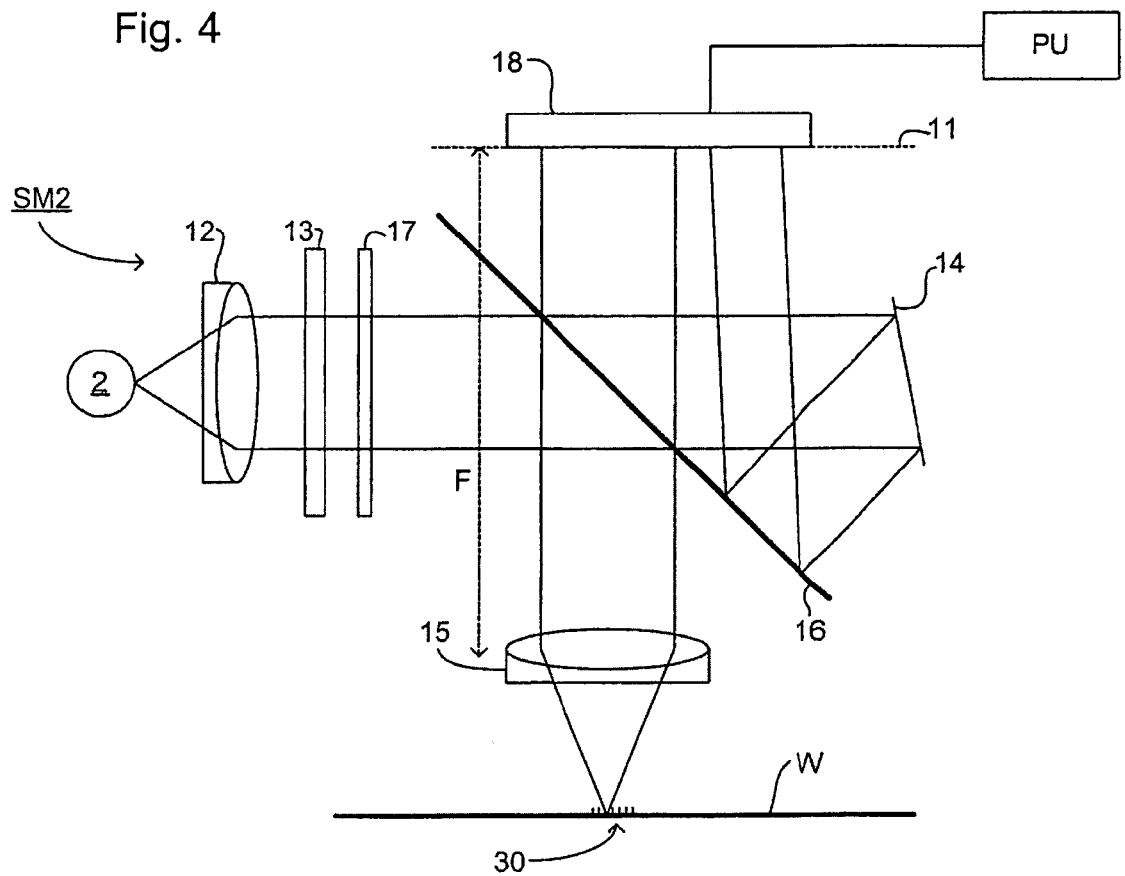
FIG. 4 depicts a second scatterometer in accordance with an embodiment of the invention.

Another scatterometer SM2 that may be used with an embodiment of the present invention is shown in FIG. 4. In this device, the radiation emitted by radiation source 2 is focused using lens system 12 through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than including a set of different filters. A grating could be used instead of interference filters.

The detector 18 may measure the intensity of scattered radiation or light at a single wavelength (or narrow wavelength range), the intensity separately at multiple wavelengths or integrated over a wavelength range. Furthermore, the detector may separately measure the intensity of transverse magnetic- and transverse electric-polarized radiation or light and/or the phase difference between the transverse magnetic- and transverse electric-polarized radiation or light.

Using a broadband radiation or light source (i.e. one with a wide range of radiation frequencies or wavelengths—and therefore of colors) is possible, which gives a large etendue, allowing the mixing of multiple wavelengths. The plurality of wavelengths in the broadband preferably each has a bandwidth of $\delta\lambda$, and a spacing of at least $2\delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a grating, which is printed such that after development, the bars are formed of solid resist lines. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
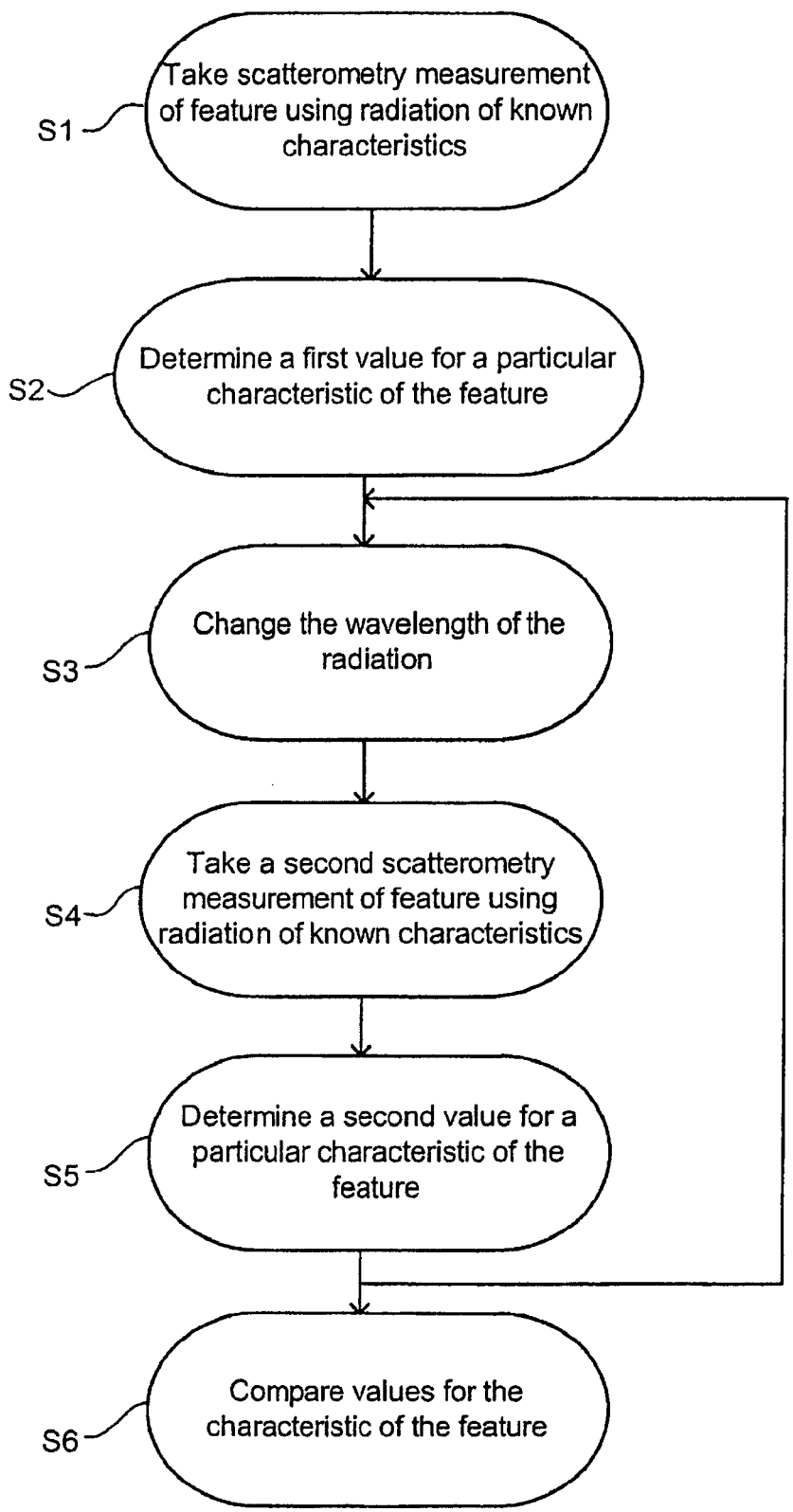
FIG. 5 shows a flowchart in accordance with an embodiment of the invention.

An embodiment of the invention is used to assess a model of a feature on a substrate and FIG. 5 depicts the procedures involved in the embodiment of the invention. At procedure S1 at scatterometry measurement of the feature is taken using radiation of known characteristics using the substrate to be assessed. The measurement is then used to determine a first value for a particular characteristic of the feature of the substrate, for example the side wall angle, at procedure S2. At procedure S3, the wavelength of the radiation is changed and then a second scatterometry measurement of the same feature is taken at procedure S4. A second value of the particular characteristic of the feature of the substrate is then determined at procedure S5. These two values of the characteristic of the feature can be compared at procedure S6. If the values are similar it indicates that the model is accurate. However, if the values differ it can indicate that the model is inaccurate. In an embodiment, it is determined whether the second value of the characteristic of the feature is within a predetermined range of the first value. The predetermined range may be a proportion of the first value.

It is also possible to make use of residuals instead of values for a particular characteristic of the feature for assessing the model. A residual is the difference between the angle resolved spectrum in the pupil plane resulting from the measured structure or profile and the angle resolved spectrum in the pupil plane resulting from the reconstructed structure of profile. A first scatterometry measurement is taken to determine a first residual. A second scatterometry is taken (after or in parallel to the first measurement) to determine a second residual. The first residual and the second residual are then compared. If the residuals are similar it indicates that the model is accurate. If the residuals differ it can indicate that the model is inaccurate. Instead residuals, also the goodness of fit can be used to assess the quality of the model, the goodness of fit being defined as the squared correlation between the measured pupil plane (i.e. the measured angle resolved spectrum) and calculated pupil plane (i.e. the angle resolved spectrum resulting from the reconstructed profile).

Figure 6:
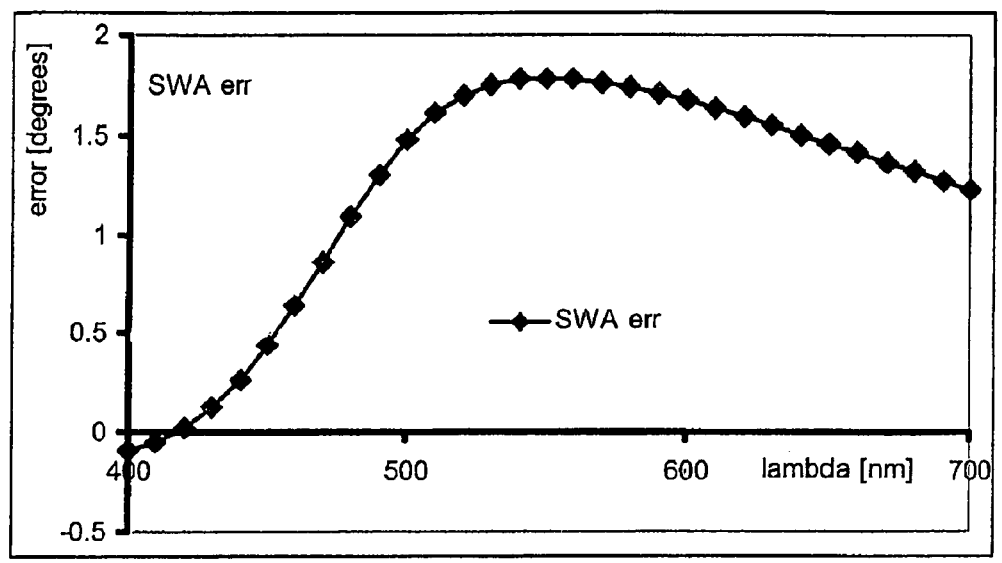
FIG. 6 depicts a graph showing results from a method according to an embodiment of the invention.

As shown in FIG. 5, the characteristic of the radiation can be repeatedly changed and repeat measurements taken. The more measurements taken, the easier it will be to determine whether the model is accurate. FIG. 6 depicts the determined side wall error (SWA-err) measured at a plurality of wavelengths. These results were obtained by using a dense resist grating of pitch 140 nm and critical dimension 55 nm. As can be seen, there is a large variation in the side wall error, which indicates that the model is not completely accurate.

In response to such a determination that the model is not accurate the model may be amended to include additional features or to adjust present features, for example the line edge roughness or top or bottom rounding. An embodiment of the invention therefore enables the accuracy of the model to be assessed.

This method may be used to assess whether a suitable number of parameters have been used in the model. For example a model which uses as few parameters as possible may be used. Scatterometry measurements are taken at a variety of wavelengths and if the results are consistent over a range of wavelengths then the number of parameters used is sufficient. However, if the results vary over the range of wavelengths additional parameters need to be added until the results are consistent over a range of wavelengths. This process may be repeated for each substrate, or alternatively just once per batch of substrates.

Although the embodiment above describes the adjustment of the wavelength of the radiation, other characteristics of the radiation could also be adjusted. For example, the angle of incidence on the substrate, the polarization or the illumination mode (TE or TM).

The wavelength of the radiation can be adjusted using conventional methods such as interference filters, acousto optical tunable filter in combination with a Xenon lamp or a supercontiniuum laser. Alternatively, multiple radiation sources, each with a different wavelength could be used. The different wavelengths of radiation may be measured either sequentially or simultaneously using, for example, an imaging spectrometer. For example a color CCD may be used to measure the intensities at three different wavelengths for a three color source. The imaging spectrometer may conveniently be located in the detection branch of the apparatus.

Figure 7:
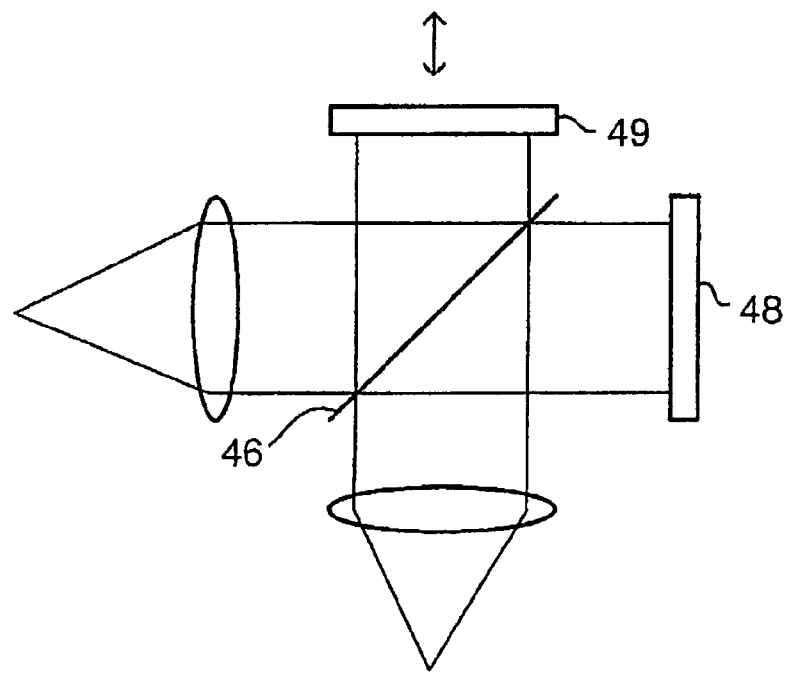
FIG. 7 depicts a Fourier transform spectrometer in accordance with an embodiment of the invention.

An alternative method of achieving multiple wavelengths is to use a Fourier Transform spectrometer. A Fourier Transform Spectrometer is shown in FIG. 7. In this spectrometer, a beam is split into two beams by a beamsplitter 46. A first beam is reflected by a fixed position mirror 48 and a second beam is reflected by a moving mirror 49. The two beams are then recombined by the beamsplitter. The two beams interfere, with the interference depending on the optical delay and hence path difference between the two beams. The intensity is then measured with the moving mirror at a plurality of positions and a spectrum determined. To determine an accurate spectrum several hundred intensities should be measured: the more intensities measured, the more accurate the spectrum. The spectrum is then subjected to a Fourier transform to obtain a measurement for each wavelength and the relevant parameter can be determined. Such a Fourier Transform Spectrometer should be used in conjunction with, for example, a white radiation or light source which generates a variety of different wavelengths of radiation. The Fourier Transform Spectrometer can be placed in the lamp house of the spectrometer or alternatively in front, or form part of the detector, 18.

In an embodiment, the detector is configured to separate the detected radiation into a plurality of sub-divisions, the radiation of each sub-division having a different value for the characteristic. Further, the inspection apparatus may also include an imaging spectrometer configured to separate the detected radiation into a plurality of sub-divisions, the radiation of each sub-division having a different value for the characteristic.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. A method comprising:
taking a first scatterometry measurement of a substrate using a first characteristic value of radiation comprising a known characteristic;
determining a first value of a characteristic of a feature of the substrate or a first residual using the first scatterometry measurement;
taking a second scatterometry measurement using a second characteristic value of the radiation;
determining a second value of the characteristic of the feature of the substrate or a second residual using the second scatterometry measurement; and
comparing the first value and the second value of the characteristic of the feature or the first residual and the second residual to determine an accuracy of a model of the feature of the substrate.

2. The method according to claim 1, further comprising changing a value of the characteristic of the radiation to a third value.

3. The method according to claim 1, further comprising:
taking a third scatterometry measurement using the third characteristic value of the radiation; and
determining a third value of the characteristic of the feature using the third scatterometry measurement;
comparing the first, second, and third values of the characteristic of the feature of the substrate.

4. The method according to claim 2, further comprising changing the value of the characteristic of the radiation to a fourth value.

5. The method according to claim 1, wherein the radiation characteristic to be changed is a wavelength of the radiation.

6. The method according to claim 1, wherein the radiation characteristic to be changed is a polarization of the radiation.

7. The method according to claim 1, wherein the radiation characteristic to be changed is an angle of incidence on the substrate.

8. The method according to claim 1, wherein the radiation characteristic to be changed is an illumination mode of the radiation.

9. The method according to claim 1, wherein the comparing comprises determining whether the second value of the characteristic of the feature is within a predetermined range of the first value of the characteristic of the feature.

10. An inspection apparatus comprising:
a radiation projector configured to project radiation onto a substrate, the radiation comprising a characteristic that comprises a plurality of values;
a high numerical aperture lens; and
a detector configured to detect the radiation reflected from a surface of the substrate,
wherein the detector is configured to separate the detected radiation into a plurality of sub-divisions, each sub-division of the plurality of sub-divisions comprising a different value for the characteristic of the radiation.

11. The inspection apparatus according to claim 10, wherein the characteristic that differs between the sub-divisions is a wavelength.

12. The inspection apparatus according to claim 10, further comprising:
an imaging spectrometer configured to separate the detected radiation into a plurality of sub-divisions, each sub-division of the plurality of sub-divisions comprising a different value for the characteristic of the radiation.

13. A lithographic apparatus comprising:
an illumination system arranged to illuminate a pattern;
a projection system arranged to project an image of the pattern on to a substrate; and
an inspection apparatus configured to measure a target on the substrate, the inspection apparatus comprising;
a radiation projector configured to project radiation onto the substrate, the radiation comprising a characteristic that comprises a plurality of values;
a high numerical aperture lens; and
a detector configured to detect the radiation reflected from a surface of the substrate,
wherein the detector is configured to separate the detected radiation into a plurality of sub-divisions, each sub-division of the plurality of sub-divisions comprising a different value for the characteristic of the radiation.

14. The inspection apparatus according to claim 13, wherein the characteristic that differs between the sub-divisions is a wavelength.

15. The inspection apparatus according to claim 13, further comprising:
an imaging spectrometer configured to separate the detected radiation into a plurality of sub-divisions, each sub-division of the plurality of sub-divisions comprising a different value for the characteristic of the radiation.

* * * * *

UNITED STATES PATENT AND TRADEMARK OFFICE
CERTIFICATE OF CORRECTION

PATENT NO.         : 8,830,472 B2                                              Page 1 of 1
APPLICATION NO.    : 12/920984
DATED              : September 9, 2014
INVENTOR(S)        : Den Boef et al.

It is certified that error appears in the above-identified patent and that said Letters Patent is hereby corrected as shown below:

In the Claims

In column 11, line 15, claim 13, after "comprising", please delete ";" and insert --:--.

Signed and Sealed this
Seventeenth Day of February, 2015

Michelle K. Lee
*Deputy Director of the United States Patent and Trademark Office*